US009743952B2

(12) United States Patent
Kiev

(10) Patent No.: US 9,743,952 B2
(45) Date of Patent: Aug. 29, 2017

(54) DEVICE AND METHOD FOR ACCESS TO INTERIOR BODY REGIONS

(71) Applicant: Jon Kiev, Vernon Hills, IL (US)

(72) Inventor: Jon Kiev, Vernon Hills, IL (US)

(73) Assignee: Jon Kiev, Lexington, KY (US)

( * ) Notice: Subject to any disclaimer, the term of this patent is extended or adjusted under 35 U.S.C. 154(b) by 45 days.

(21) Appl. No.: 14/809,214

(22) Filed: Jul. 25, 2015

(65) Prior Publication Data

US 2016/0235436 A1 Aug. 18, 2016

Related U.S. Application Data

(63) Continuation-in-part of application No. 14/624,818, filed on Feb. 18, 2015.

(51) Int. Cl.
*A61M 31/00* (2006.01)
*A61B 17/34* (2006.01)
(Continued)

(52) U.S. Cl.
CPC .... *A61B 17/3415* (2013.01); *A61B 17/32093* (2013.01); *A61B 17/3474* (2013.01);
(Continued)

(58) Field of Classification Search
CPC .. A61M 2025/0188; A61M 2025/0681; A61M 2039/062; A61M 2039/064; A61M 25/01; A61M 25/09; A61M 29/02; A61M 39/06; A61M 25/0625; A61M 2005/325; A61M 2025/0008; A61M 2039/244; A61M 25/0043; A61M 25/007; A61M 25/0668; A61M 25/0693; A61M 25/0618; A61M 25/0662; A61M 25/09041; A61M 2025/0687; A61M 2025/09125; A61M 25/0105; A61M 25/0631; A61M 25/0637; A61M 25/0643; A61M 5/3257; A61B 17/3145; A61B 17/3421; A61B 17/3431; A61B 17/3474; A61B 17/3496; A61B 17/32093; A61B 2017/3437; A61B 2017/346; A61B 2017/00809; A61B 17/34

See application file for complete search history.

(56) References Cited

U.S. PATENT DOCUMENTS 5,342,382 A 8/1994 Brinkerhoff et al.
5,522,833 A 6/1996 Stephens et al.
(Continued)

FOREIGN PATENT DOCUMENTS

CN 2252603 4/1997
GB WO 2014006403 A1 * 1/2014 ........ A61M 25/0026

*Primary Examiner* — Bhisma Mehta
*Assistant Examiner* — Nawal Boufrou
(74) *Attorney, Agent, or Firm* — Evan D. Linderman

(57) ABSTRACT

A device and method is provided to gain access to interior body regions. The system includes a safety needle assembly, a blade assembly, an obturator assembly, and a dilator assembly. The safety needle assembly accesses an interior body region, after which the blade assembly expands the pathway created by the safety needle assembly. The obturator then further expands the pathway and delivers the dilator assembly to the desired location. The safety needle assembly, obturator assembly, and blade assembly are removed, leaving the dilator assembly in place for future procedures.

7 Claims, 13 Drawing Sheets

(51) Int. Cl.
*A61B 17/3209* (2006.01)
*A61B 17/00* (2006.01)
(52) U.S. Cl.
CPC ..... *A61B 17/3496* (2013.01); *A61B 2017/00809* (2013.01); *A61B 2017/346* (2013.01)

(56) References Cited

U.S. PATENT DOCUMENTS

| | | | |
|---|---|---|---|
| 5,843,115 A | 12/1998 | Morejon | |
| 6,017,356 A * | 1/2000 | Frederick | A61B 17/3417 604/264 |
| 6,056,766 A * | 5/2000 | Thompson | A61B 17/3421 606/108 |
| 6,156,006 A | 12/2000 | Brosens et al. | |
| 6,402,770 B1 | 6/2002 | Jessen | |
| 6,613,063 B1 | 9/2003 | Hunsberger | |
| 7,344,519 B2 | 3/2008 | Wing et al. | |
| 7,419,496 B2 | 9/2008 | Staudner | |
| 8,419,764 B2 | 4/2013 | Begg | |
| 8,801,741 B2 | 8/2014 | Ahlberg et al. | |
| 2007/0270819 A1 | 11/2007 | Justis et al. | |
| 2008/0009894 A1 | 1/2008 | Smith | |
| 2012/0116418 A1 * | 5/2012 | Belson | A61B 17/0469 606/139 |

* cited by examiner

DEVICE AND METHOD FOR ACCESS TO INTERIOR BODY REGIONS

CROSS-REFERENCE TO RELATED APPLICATIONS

Pursuant to 35 U.S.C. §120, this application is a continuation-in-part of, and claims priority to, co-pending U.S. patent application Ser. No. 14/624,818, filed Feb. 18, 2015, which is incorporated by reference herein in its entirety.

TECHNICAL FIELD

The present invention relates to devices and methods to access interior body regions. More particularly, it relates to devices and methods used to create space to insert a tube into a patient.

BACKGROUND

Embodiments of the invention relate to devices to create access to interior body regions and methods of using the devices.

There are many instances in which a practitioner must access the chest, abdomen, or pelvis, and insert a drainage tube, or chest tube. Examples of these instances include: collapsed lung, lung infection, bleeding in the chest cavity, fluid or air buildup due to other medical conditions or trauma, and prior surgery.

The traditional way of inserting a chest tube begins with the practitioner prepping the side of the body for the chest tube by sterilizing the area. Using a scalpel, the practitioner then makes a small incision (skin nick), between the ribs closest to the desired location in the chest. Then, using a combination of blunt dissection and surgical clamps, the practitioner will slowly open the space and extend it into the chest cavity. Once the practitioner confirms she has reached the desired space, the chest tube is inserted and sutured in place to prevent slippage.

Critics claim that the traditional method of chest tube insertion is barbaric and does not take advantage of advances in technology that can make the insertion process safer and more effective. Some companies have designed devices, called trocars, to facilitate safer and easier chest tube placement without using multiple, separate components.

Many groups of trocars include a combination of a safety needle, an obturator and a dilator. The doctor advances the device against the skin and interior body regions using the safety needle. As the doctor advances the device through the body, the obturator expands the pathway created by the safety needle. When the device reaches the desired area, the practitioner removes the safety needle and the obturator from the dilator, leaving the dilator in place. The practitioner then pushes the chest tube through the dilator and removes the dilator, leaving the chest tube in the desired location.

Problems arise with these types of trocars, however, because the obturator does not actually work very well in expanding the pathway created by the relatively small safety needle. The skin provides a tough membrane that resists expansion, and additional skin nicks (using a separate scalpel) are required around the safety needle to allow the obturator to properly expand the skin layer and continue to penetrate deeper into the body.

To address this issue, other groups of trocars employ a retractable blade instead of a safety needle. The blade is used to create a larger skin nick and advance through other tissues as needed until reaching the desired location. The obturator easily expands the pathway as it passes through the skin layer while the practitioner advances the device, and then the blade is retracted and the blade/obturator combination is removed, leaving the dilator in place for the chest tube.

While these groups of trocars address the issue of requiring an additional scalpel to allow the obturator to expand the skin layer, they do not include the safety needle that prevents the doctor from progressing too quickly or too far and causing harm to the patient. Without the safety needle as part of the system, the patient is at a greater risk of complications.

What is needed in the market is an all-in-one trocar device that provides the ability to create a skin nick and maintain safety as the device is inserted deeper into the body, while quickly accessing the desired location for chest tube placement.

BRIEF SUMMARY OF THE INVENTION

Benefits achieved in accordance with principles of the disclosed invention include a device that provides access to interior body regions.

Some aspects of the present invention relate to a safety needle assembly, a blade assembly, an obturator assembly, and a dilator assembly. The safety needle assembly, blade assembly, obturator assembly, and dilator assembly are assembled to create an access device.

In some aspects of the present invention, the blade assembly includes multiple blades, while in other aspects of the present invention, the blade assembly includes a single blade.

In other aspects of the present invention, the safety needle assembly includes a hub through which fluid may be drawn in order to confirm the device has reached the proper location within the body.

In further aspects of the present invention, the blade assembly and safety needle assembly are longitudinally coaxial, while in still further aspects of the present invention, the blade assembly and safety needle assembly are not longitudinally coaxial.

Yet other aspects of the present invention relate to a method of accessing interior body regions in which the safety needle assembly is advanced through skin and into interior body regions to create a pathway. The blades of the blade assembly are deployed and the blade assembly is advanced into the skin to create a skin nick, after which the blades are retracted. The access device is then advanced into the tissue, and the obturator assembly increases the diameter of the pathway created by the safety needle. After the access device is in the proper location, the safety needle assembly, blade assembly, and obturator assembly are removed from the dilator assembly, leaving the dilator assembly in the body to provide a conduit through which other devices may be inserted.

BRIEF SUMMARY OF THE DRAWINGS

The accompanying drawings, which are incorporated in and form a part of the specification, illustrate example embodiments and, together with the description, serve to explain the principles of the invention. In the drawings.

DETAILED DESCRIPTION

Figure 1:
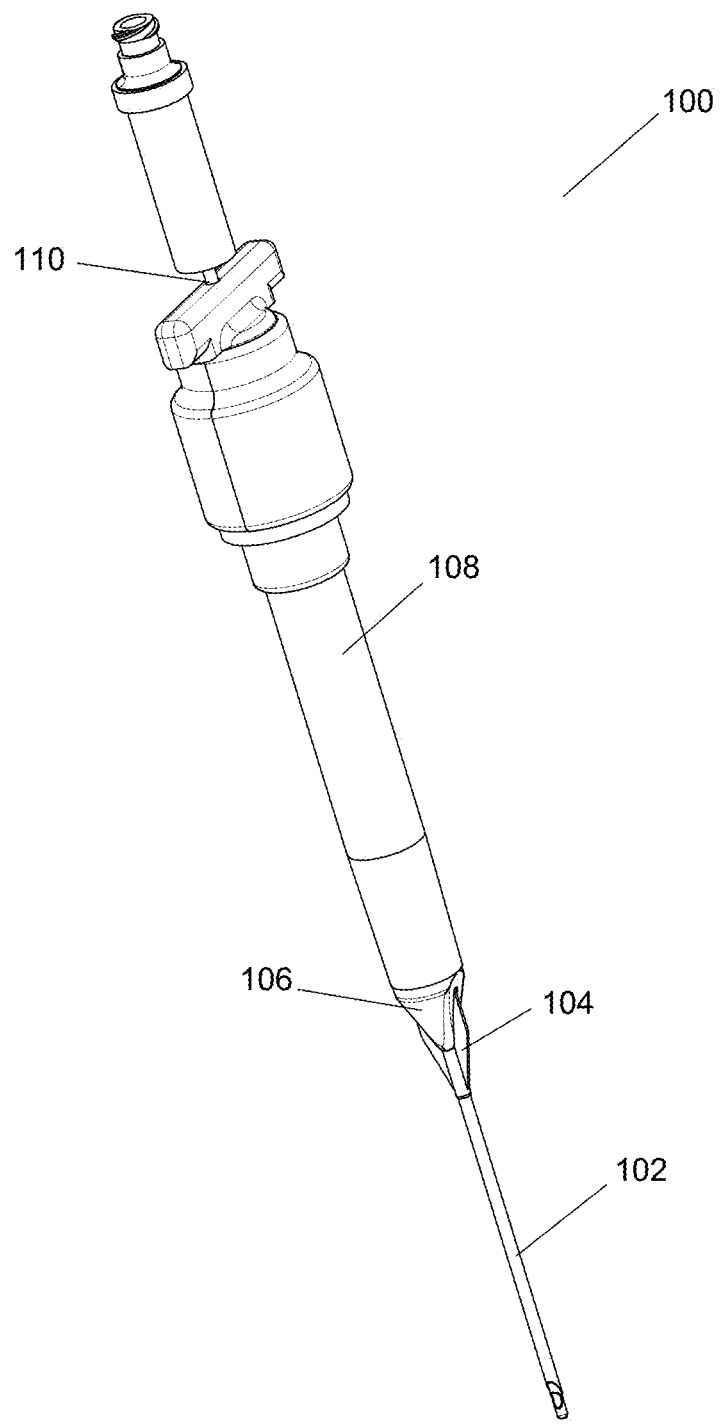
FIG. 1 illustrates an insertion device according to aspects of the present invention.

FIG. 1 illustrates an insertion device according to aspects of the present invention.

As shown in the figure, insertion device 100 includes safety needle 102, blade assembly 104, obturator assembly 106, dilator assembly 108, and handle hole 110.

Specific aspects of safety needle 102, blade assembly 104, obturator assembly 106, and dilator assembly 108 will be further described with reference to FIGS. 2, 3, 4, and 8, respectively.

In general, insertion device 100 is assembled by inserting safety needle assembly 102 through handle hole 110 and into blade assembly 104 until safety needle assembly 102 is distal to the distal end of blade assembly 104. Then, the combination of safety needle assembly 102 and blade assembly 104 is inserted through obturator assembly 106. Then, obturator assembly 106, blade assembly 104, and safety needle assembly 102 are connected to dilator assembly 108. A more detailed description of the assembly and operation of insertion device 100 will be further described with reference to FIGS. 2-8.

Figure 2:
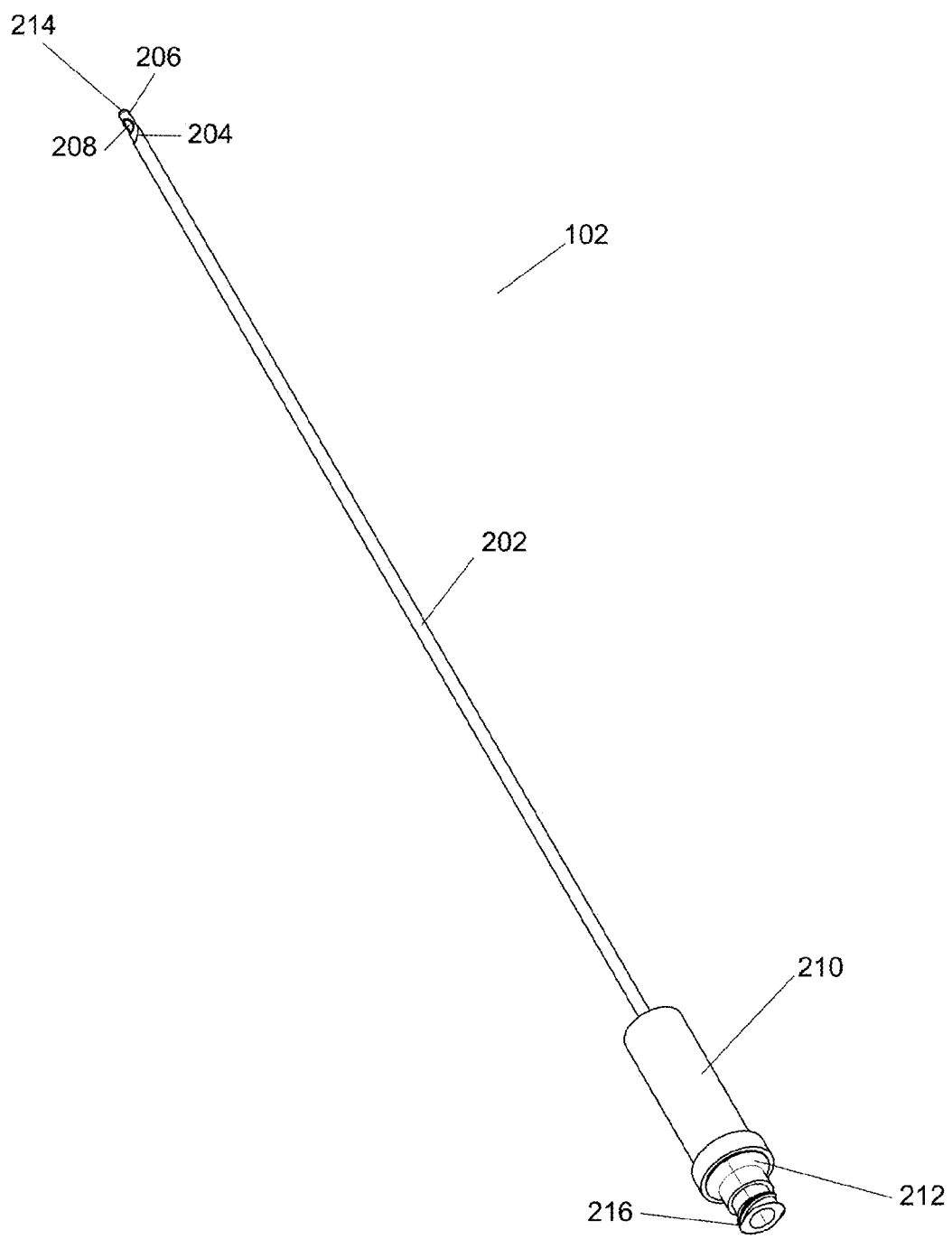
FIG. 2 illustrates a safety needle according to aspects of the present invention.

FIG. 2 illustrates a safety needle according to aspects of the present invention.

As shown in the figure, safety needle 102 includes cannula 202, cannula tip 204, stylet 206, stylet port 208, stylet tip 214, housing 210, hub 212, and connection means 216.

Cannula 202 is preferably constructed from a generally rigid material, such as metal or plastic, but other rigid materials may be considered. It may be extruded, welded, molded, or manufactured by any other method that would result in a generally rigid material. Cannula 202 is connected to hub 210 such that there is no relative movement between hub 210 and cannula 202. The connection may be via any mechanical means (a non-limiting example of which includes overmolding), adhesive means (a non-limiting example of which includes UV adhesive), or any other means that would create a bond between housing 210 and cannula 202 to prevent relative motion between the two components.

Cannula tip 204 is designed to penetrate through tissue, and therefore it is relatively sharp. Cannula tip 204 may be manufactured by any known means to create a beveled tip, a conical tip, a crown tip, or any other geometry that is known in the art to provide a tip sharp enough to penetrate tissue.

Stylet 206 is preferably constructed from a generally rigid material, such as metal or plastic, but other rigid materials may be considered. It may be extruded, welded, molded, or manufactured by any other method that would result in a generally rigid material. Stylet 206 is connected to housing 210 such that there may be relative motion between the two components. The outer diameter of stylet 206 is smaller than the inner diameter of cannula 202, and stylet 206 is slidably positioned inside of cannula 202.

Figure 6:
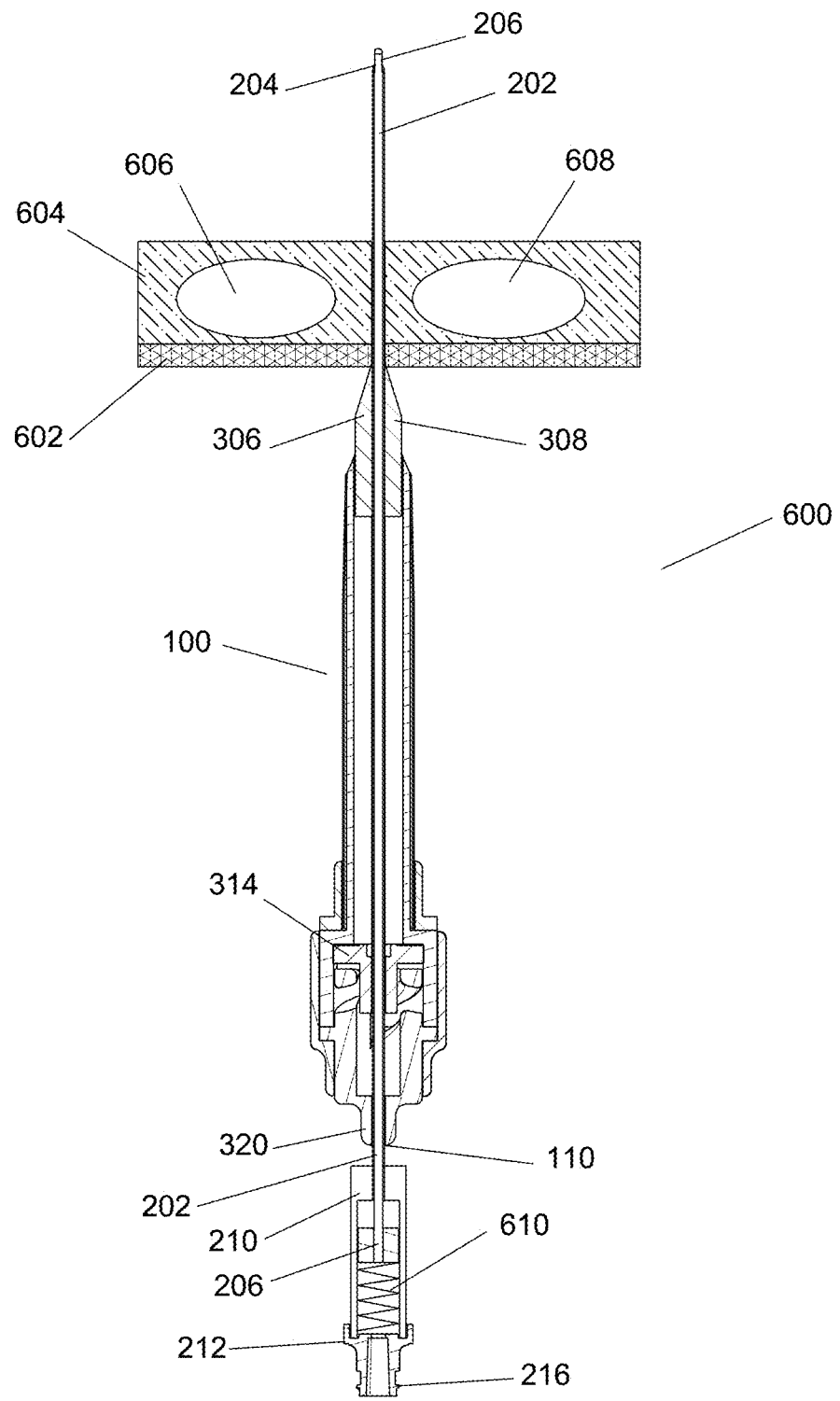
FIG. 6 illustrates a first step in inserting the insertion device according to aspects of the present invention.

Referring now to FIG. 6, housing 210 is a generally rigid component that is either machined or molded out of plastic. Housing 210 is connected to cannula 202 and to hub 212. The center of housing 210 is open to accommodate spring 610 and allow spring 610 to be compressed and uncompressed during use.

Stylet 206 is connected to spring 610 via any mechanical, chemical or adhesive means that would create a bond between the two components. In an alternate embodiment, stylet 206 and spring 610 may both be connected to an intermediate part, such that stylet 206 and spring 610 are effectively bonded together. Spring 610 is connected to housing 210 and hub 212 via any mechanical, chemical or adhesive means that would create bond between the two components. In yet another alternate embodiment, spring 610 may freely float in between stylet 206 and hub 212 such that no bond between components is required.

Referring back to FIG. 2, stylet tip 214 is designed to avoid penetrating through tissue, and therefore it is relatively blunt and closed at the distal end. Stylet tip 214 may be manufactured by any known means to create a curved tip, a bullet tip, a flat tip, or any other geometry that is known in the art to create a closed distal tip that will avoid penetrating tissue.

Stylet port 208 is an open section in stylet 206 that is proximal to stylet tip 214 and distal to cannula tip 204 when spring 610 is uncompressed. Stylet port 208 may be manufactured by traditional grinding or machining techniques or by more advanced techniques, including electric discharge machining (EDM), chemical etching, or laser machining.

Referring back to FIG. 6, hub 212 is a generally rigid component that is either machined or molded out of plastic. Hub 212 is connected to spring 610 and to housing 210. Hub 212 includes connection means 216 such that hub 212 may be connected to an external source for fluid drainage or administration.

Referring back to FIG. 2, connection means 216 is shown as a threaded connection, however any suitable connection means (a non-limiting example of which includes a snap fit) that provide for connection of a fluid drainage or administration device is acceptable.

Referring to FIGS. 2 and 6, in operation, a user grasps hub 210 or another component that may be coupled to hub 210 and advances safety needle assembly 102 toward a patient's skin. The first component of safety needle assembly 102 that contacts the skin is stylet tip 214. As the user continues to push safety needle assembly 102 into the skin, the blunt stylet tip 214 transfers the pushing force through stylet 206, compresses spring 610, causes cannula 202 to move relative to stylet 206, and allows cannula tip 204 to move toward the skin.

When the pushing force is sufficient enough, cannula tip 204 will contact the skin and the sharp tip will penetrate the skin and soft tissues underneath the skin. When cannula tip 204 reaches an area of little or no resistance, spring 610 will uncompress, allowing stylet 206 to move forward again such that stylet tip 214 is distal to cannula tip 204, and stylet port 208 is exposed to the area. Areas of little or no resistance include fluid (or air) filled spaces such as the plerua, lungs, or any other fluid filled space the user desires to reach.

To confirm that safety needle assembly 102 is in the correct location, the user may connect a fluid drainage device to connection means 216 and use the fluid drainage device to pull fluid or air from the area as means of confirmation. Fluid drainage devices that may be used include syringes, suction canisters, wall suction, and any other means that may operate to pull fluid from the patient to confirm appropriate placement of safety needle assembly 102.

Figure 3:
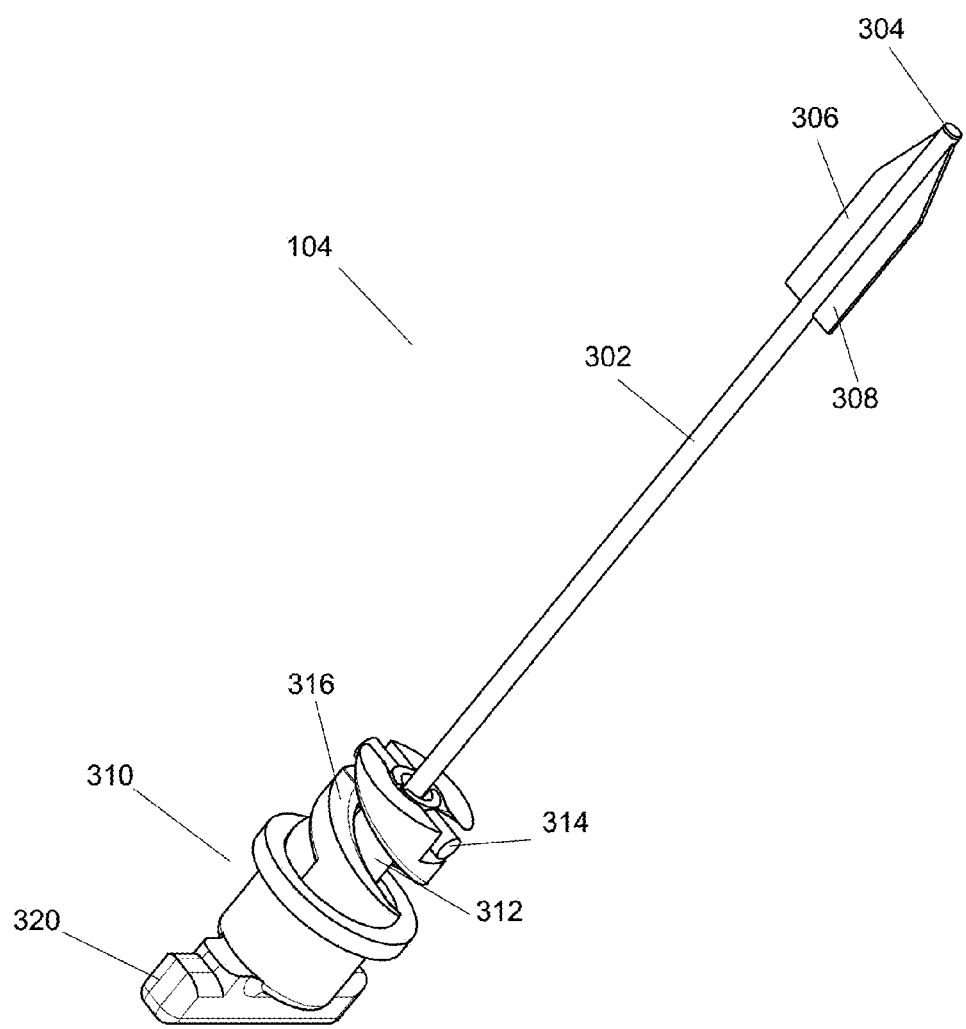
FIG. 3 illustrates a blade assembly according to aspects of the present invention.

FIG. 3 illustrates a blade assembly according to aspects of the present invention.

As shown in the figure, blade assembly 104 includes shaft 302, distal tip 304, blades 306 and 308, handle 310, follower shaft 312, and follower 314.

Shaft 302 is a rigid tube and is preferably made of metal, however any other rigid material would suffice. Shaft 302 is connected to follower shaft 314 such that there is no relative motion between the two components. The connection may be made via mechanical, adhesive, or chemical means. Shaft 302 is also connected to blades 306 and 308. The connection is preferably a welded connection, however other connection means may be employed. For example, shaft 302 may contain one or more slots at its distal end and blades 306 and 308 may contain one or more matching slots such that blades 306 and 308 may be assembled on to shaft 302 by sliding slotted sections of blades 306 and 308 on to the corresponding slots at the distal end of shaft 302.

Distal tip 304 is at the distal end of shaft 302 and is operable to provide a leading edge for blades 306 and 308. Distal tip 304 may be produced by any conventional tip grinding or finishing process, and it may be a beveled tip, a conical tip, a crown tip, or any other tip that would provide an appropriate leading edge for blades 306 and 308.

Blades 306 and 308 are preferably constructed from metal, more preferably from stainless steel, however any material suitable for medical applications would suffice. Blades 306 and 308 are operable to cut the skin of a patient, and as such are sufficiently sharp to cut skin. The specific shape, grind angles, and tip angles may be of any dimensions such that the effect of cutting skin may be accomplished. Blades 306 and 308 are attached to shaft 302 as previously described.

Handle 310 includes handle top 320 and cam 316. Handle 310 is preferably made of plastic via either machining or molding, however any other suitable materials or manufacturing methods may be used. Handle top 320 is designed to be gripped by a user in order to rotate handle 310 relative to follower shaft 312 and follower 314. Rotating handle top 320 and the motion of follower shaft 312 and follower 314 will be further discussed with reference to operation of blade assembly 104 below. Cam 316 is a slot within handle 310 in which follower 314 travels. Cam 316 may be constructed with any geometry that will provide the desired motion of follower 314.

Follower 314 and follower shaft 312 are both preferably made of plastic via either machining or molding, however any other suitable materials or manufacturing methods may be used. In some embodiments, follower 314 and follower shaft 312 may be a single component, however they are shown here as two separate components. Follower 314 and follower shaft 312 are bonded together by any suitable means that will effectively prevent relative motion between the two components. In addition, shaft 302 is bonded to follower 314 and follower shaft 312 to prevent relative motion between the three components.

In operation, a user will turn handle 310 to effect a linear movement of shaft 302. The user will grasp handle top 320 with one hand and dilator assembly 108 (not shown) with the other hand. Handle 310 therefore only rotates, and does not move in a linear direction when handle top 320 is turned. FIG. 3 shows blade assembly 104 with blades 306 and 308 fully deployed. To retract blades 306 and 308, the user would turn handle top 320 in the appropriate direction. Turning handle top 320 causes cam 316 to rotate. As cam 316 rotates, follower 314 moves in a linear manner such that follower 314 moves closer to handle top 320. To deploy blades 306 and 308, the user would turn handle top 320 in the opposite direction.

Figure 4:
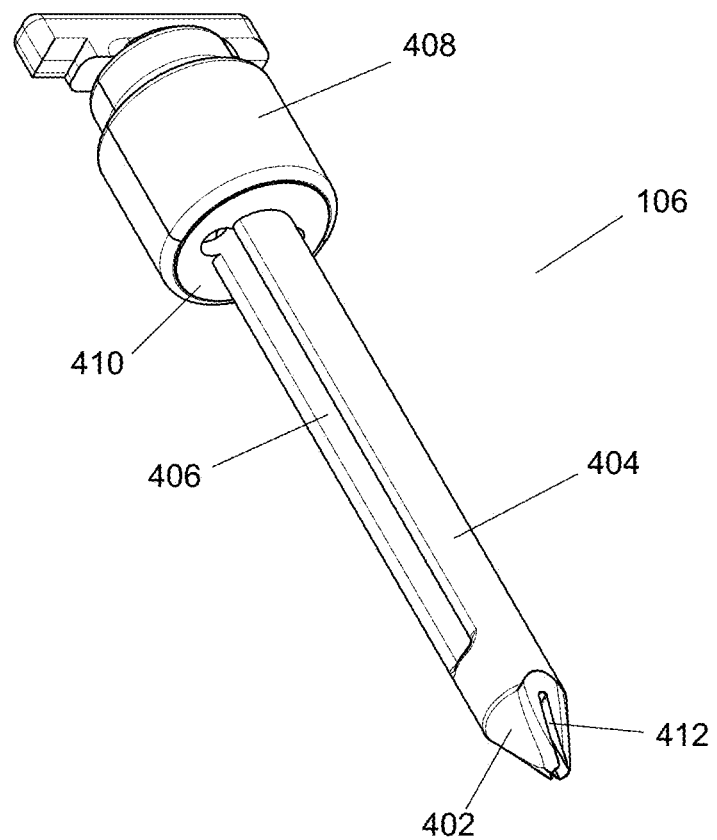
FIG. 4 illustrates an obturator assembly according to aspects of the present invention.
Figure 5:
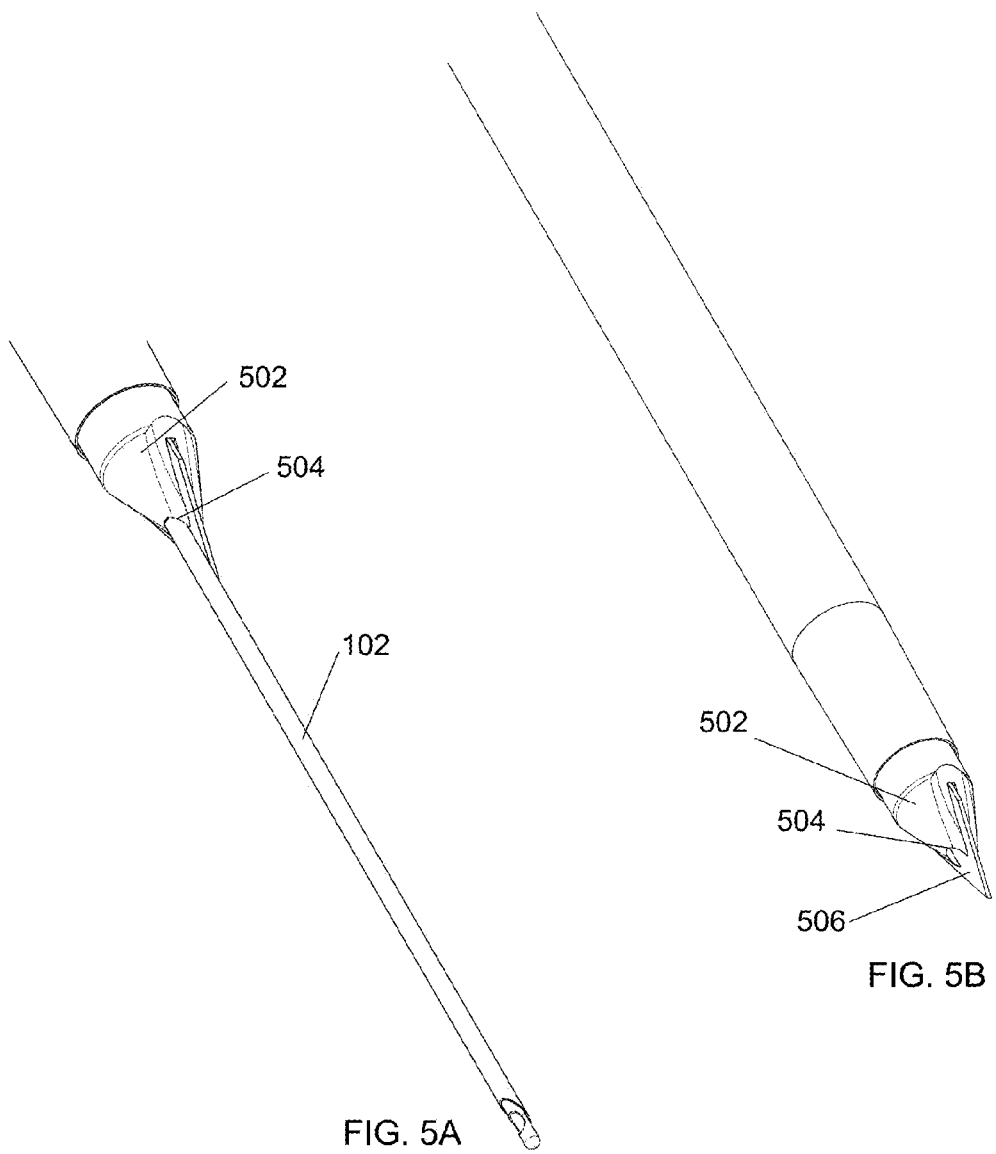
FIGS. 5A-B illustrate an alternate embodiment of a blade assembly and an obturator assembly according to aspects of the present invention.

FIG. 4 illustrates an obturator assembly according to aspects of the present invention.

As shown in the figure, obturator assembly 106 includes obturator tip 402, obturator shaft 404, handle cover 408, and obturator hub 410. All components of obturator assembly 106 are preferably made from plastic via either machining or molding processes, however any suitable material or manufacturing method may be used to create the component.

Obturator tip 402 is operable to enlarge an opening in the skin, and includes blade slot 412. Blade slot 412 is operable to provide a pathway for blades 306 and 308 to be deployed beyond the distal-most portion of obturator tip 402 and to be fully retracted within obturator tip 402. Obturator tip 402 is connected to obturator shaft 404 by any suitable means that would prevent relative motion between the two components. In an alternate embodiment, obturator tip 402 and obturator shaft 404 may be a single component.

Obturator shaft 404 is operable to travel within the enlarged opening created by obturator tip 402, and includes obturator slot 406. Obturator slot 406 is present to reduce weight and manufacturing costs. In an alternate embodiment, obturator slot 406 may be omitted entirely such that obturator shaft 404 is a continuous tube with no openings in its diameter.

Obturator hub 410 is connected to obturator shaft 404 by any means that would create a bond to prevent relative motion between the two components. Obturator hub 410 is operable to constrain the linear motion of follower 314 (not shown), such that blades 306 and 308 can only extend from obturator tip 402 by a defined distance.

Handle cover 408 is operable to attach to obturator hub 410 and cover cam 316 (not shown) such that a user cannot interfere with the operation of cam 316. Handle cover 408 may be a single component or multiple components that can be attached together. Additionally, in an alternate embodiment, handle cover 408 and obturator hub 410 may be a single component.

Returning to FIG. 1, and with reference to FIGS. 2-4, assembly of insertion device 100 will be described.

To assemble insertion device 100, safety needle 102 is inserted through handle hole 110 and extends through the inner diameter of shaft 302 of blade assembly 104, extending beyond distal tip 304. The combination of safety needle 102 and blade assembly 104 is inserted through the inner diameter of obturator shaft 404 until obturator hub contacts cam 316 of blade assembly 104. Handle cover 408 is then installed to cover cam 316. Finally, the entire assembly is inserted through the inner diameter of dilator assembly 108 to complete the assembly process. There are no connections between dilator assembly 108 and the rest of the components; a simple press-fit interaction serves to keep dilator assembly 108 connected to the rest of the components. In an alternate embodiment, dilator assembly 108 may detachably lock to obturator assembly 106. Dilator assembly 108 will be further described with reference to FIGS. 6-8.

FIGS. 5A-B illustrate an alternate embodiment of a blade assembly and an obturator assembly according to aspects of the present invention.

As shown in the figures, obturator tip 502 includes cutout 504 to accommodate safety needle 102. A blade slot similar to blade slot 412 provides space for blade 506 to deploy and retract.

In this embodiment, blade 506 is a single blade instead of multiple blades as previously described. The single blade may be attached to shaft 302 by any means previously described. If attaching multiple blades to the outer diameter of shaft 302 is difficult to accomplish, this alternate embodiment may be employed, as methods to attach a single blade to a shaft are well known in the art.

In attaching blade 506 to shaft 302, a difficulty is encountered as safety needle 102 and blade 506 cannot be longitudinally coaxial with each other as is possible with the multiple blade design. Therefore, it is necessary to create cutout 504 to accommodate safety needle assembly 102. In this embodiment, blade 506 slides along the outer diameter of safety needle assembly 102.

Testing has proven that, even though safety needle 102 is not concentric with respect to the rest of insertion device 100, the ability of blade 506 to enlarge the pathway created by safety needle 102 is not impacted, and the performance of insertion device 100 is not diminished.

In yet another alternate embodiment, and with further reference to FIGS. 3-4, it may be desirable to eliminate the need to turn handle 320 to deploy and retract blades 306 and 308. In such an embodiment, blade assembly 104 may contact a spring that rests on obturator hub 410. There may be a window in handle cover 408 such that the user's finger could reach blade assembly 104 through the window. Access to blade assembly 104 may also be available via obturator slot 406. When the user desires to deploy the blades, the user would extend a finger into the window and press down on blade assembly 104, compressing the spring and exposing the blades. After using the blades, the user would remove his/her finger from blade assembly 104, which would then automatically retract blades 306 and 308 into obturator assembly 106 as the spring uncompressed.

FIG. 6 illustrates a first step in inserting the insertion device according to aspects of the present invention.

As shown in the figure, system 600 includes skin 602, soft tissue 604, and ribs 606 and 608.

Figure 7:
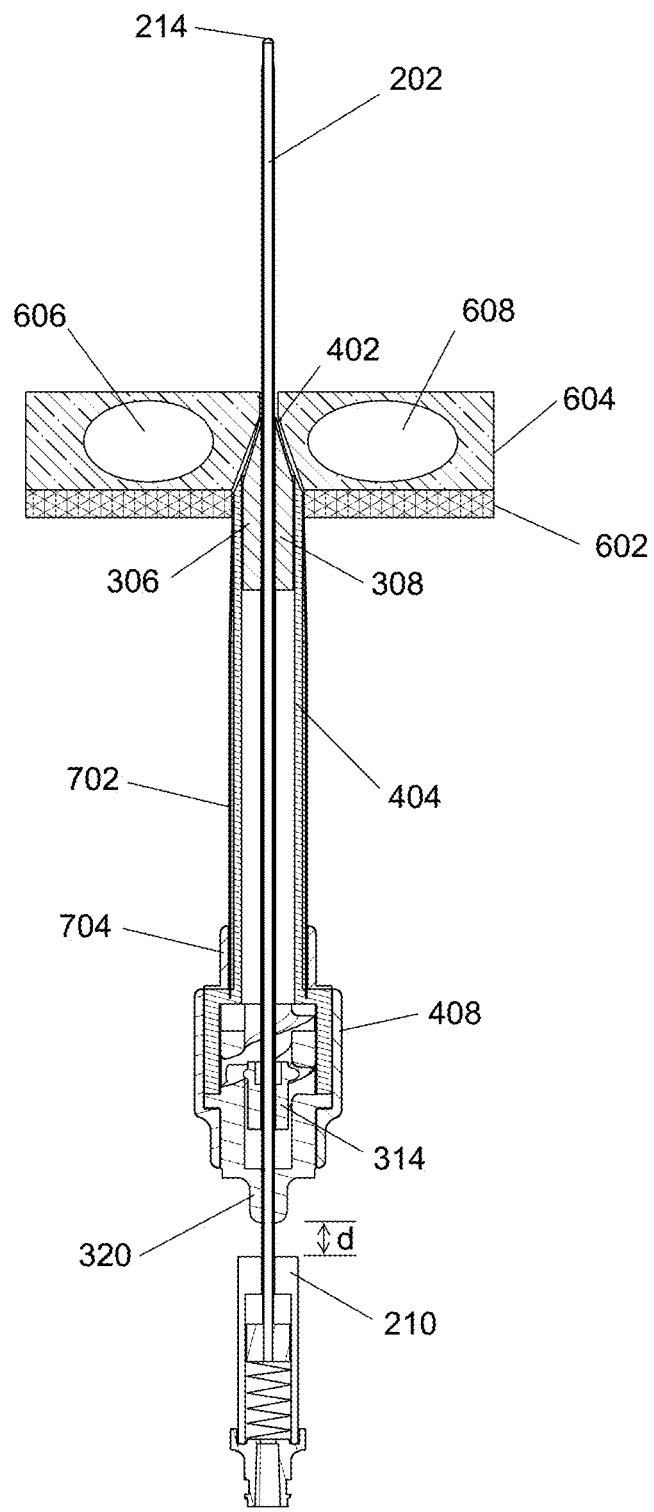
FIG. 7 illustrates a second step in inserting the insertion device according to aspects of the present invention.

Prior to inserting device 100 into a patient, a user will palpate the skin to determine the appropriate insertion point between ribs 606 and 608. Once the desired location is found, the user begins to insert insertion device 100. While not shown in FIG. 6, when first inserting insertion device into the patient, blades 306 and 308 are not deployed and are located within obturator assembly 106 (similar to the device as shown in FIG. 7).

When inserting insertion device 100 into the patient, safety needle 102 is the first component to contact the patient's skin 602. As described with reference to FIG. 2, pushing safety needle 102 against the patient's skin 602 causes stylet 206 to retract, exposing the sharp cannula tip 204 to the skin. As the user continues to push, cannula tip 204 cuts through skin 602 and soft tissue 604. Soft tissue 604 may include muscle, fat, fascia, or any other soft tissues with which safety needle 102 may come in contact with during the procedure.

A skilled user can generally tell when the desired location is reached, as a distinct decrease in resistance occurs. The decrease in resistance is an indication that safety needle 102 has reached the desired, fluid-filled location. To confirm that safety needle 102 has reached the desired location, the user will attach a fluid drainage device to hub 212 via connection means 216. The user will then attempt to drain fluid from the area. If the desired fluid is drawn from the area, the user may continue with the procedure. If the desired fluid is not drawn from the area, the user may need to continue in attempts to find the desired location.

Assuming the desired fluid has been located, the user then deploys blades 306 and 308 by turning handle 320 until handle 320 cannot be turned any more, meaning blades 306 and 308 are fully deployed. The user then advances insertion device 100 until blades 306 and 308 enter skin 602 to create a skin nick. If desirable, after creating the skin nick, the user may pull insertion device back such that blades 306 and 308 are not in skin 602, rotate insertion device 100 90 degrees, and then advance insertion device again until blades 306 and 308 enter skin 602. After one or more skin nicks are created, the user turns handle 320 in the opposite direction until it cannot be turned any more, meaning blades 306 and 308 are fully retracted. The user can then further advance insertion device 100, which is further described with reference to FIG. 7.

In an alternate method, the user may deploy blades 306 and 308 first, create a skin nick, and then retract blades 306 and 308. The user may then proceed with inserting safety needle 102 into the patient as previously described, or the user may decide to forego using safety needle 102 and instead insert obturator assembly 106, blade assembly 104, and dilator assembly 108 into the desired space within the patient.

FIG. 7 illustrates a second step in inserting the insertion device according to aspects of the present invention.

As shown in the figure, insertion device 100 is pushed further into the patient. As insertion device 100 advances, obturator tip 402 expands the pathway created by safety needle 102 and the one or more skin nicks. The user holds safety needle 102 with one hand while advancing obturator assembly 106, blade assembly 104, and dilator assembly 108. The distance between housing 210 and handle 320, noted as "d", will increase as the user continues to advance obturator assembly 106, blade assembly 104, and dilator assembly 108.

When obturator tip 402 reaches stylet tip 214, the user may stop advancement. The user may use an appropriate imaging technique to determine when obturator tip 402 reaches stylet tip 214. In an alternate embodiment, cannula 202 may include an indicator mark, such that when handle 320 no longer covers the indicator mark, obturator tip 402 has reached stylet tip 214.

The user can then remove components to prepare the patient for insertion of a catheter. Safety needle assembly 102, blade assembly 104, and obturator assembly 106 may all be removed from dilator assembly 108 at the same time. To remove the components, the user will grip dilator shaft 702 with one hand and handle cover 408 with the other hand.

Dilator shaft 702 will be further described with reference to FIG. 8. While holding dilator shaft 702 steady, the user will pull back on handle cover 408. This will serve to detach Safety needle assembly 102, blade assembly 104, and obturator assembly 106 from the press-fit connection to dilator assembly 108. As the user continues to pull back on handle cover 408, all components will be removed from dilator assembly 108, leaving dilator assembly 108 in the body.

Figure 8:
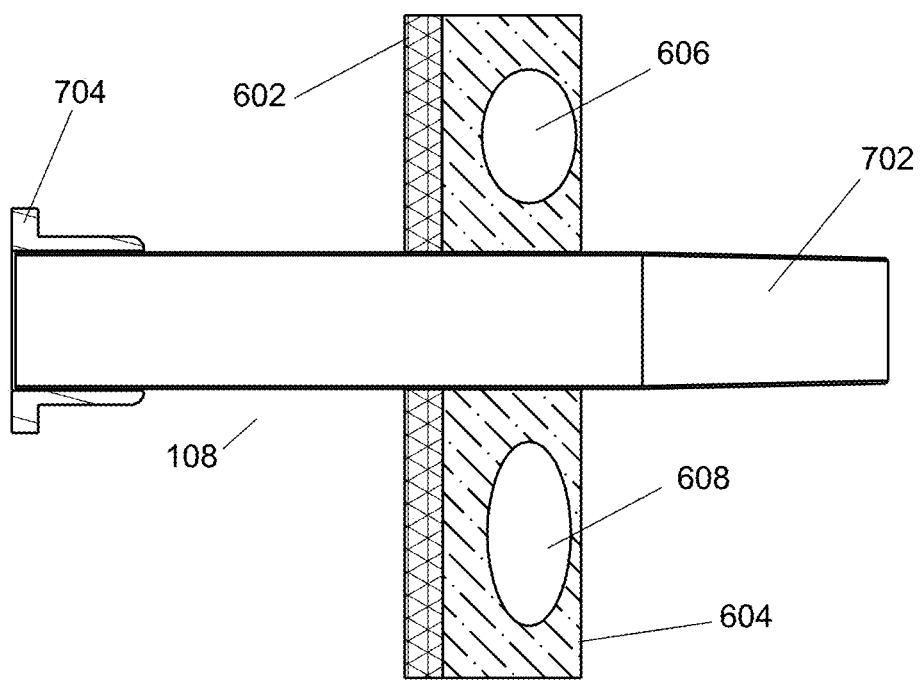
FIG. 8 illustrates a final step in inserting the insertion device according to aspects of the present invention.

FIG. 8 illustrates a final step in inserting the insertion device according to aspects of the present invention.

As shown in the figure, dilator assembly 108 is in the patient. Dilator assembly 108 includes dilator shaft 702 and dilator hub 704. Dilator shaft 702 is preferably made of plastic and may be extruded, molded, or manufactured in any other known way to create the desired geometry. Dilator hub 704 is also preferably made of plastic by any known method to create the desired geometry. Dilator hub 704 and dilator shaft 702 are connected by any known methods that would serve to prevent any relative motion between the two components.

At this point in the procedure, the user will typically place a catheter through the lumen of dilator shaft 702 to reach the desired location within the body. Essentially, dilator shaft 702 is simply a conduit through which another device (i.e., a catheter) is placed. Once the catheter is placed in the desired location, dilator assembly 108 is removed from the patient. The user then completes the procedure by closing skin 602 around the catheter.

Figure 9:
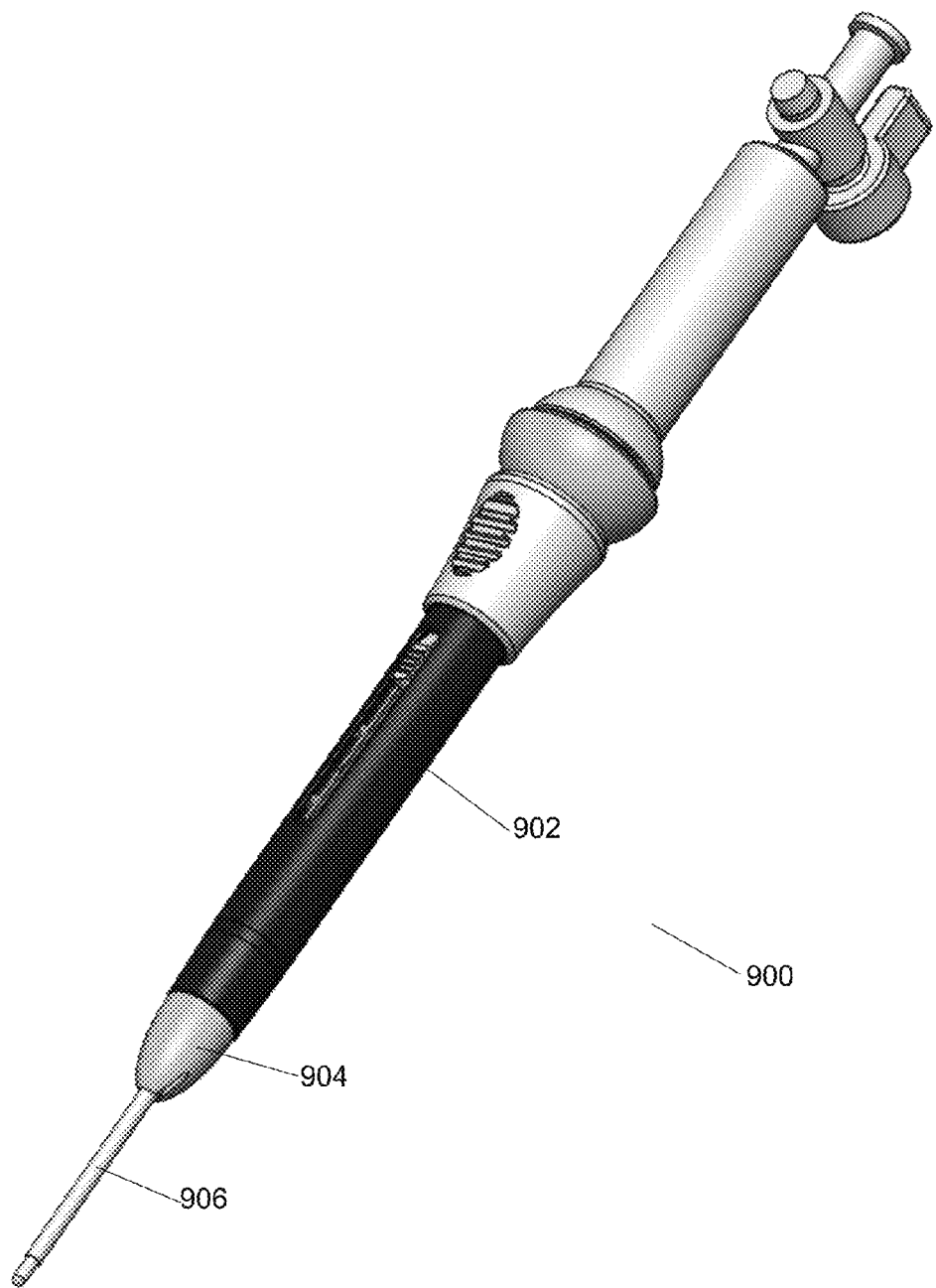
FIGS. 9-10 illustrate an alternate embodiment of an insertion device according to aspects of the present invention.
Figure 10:
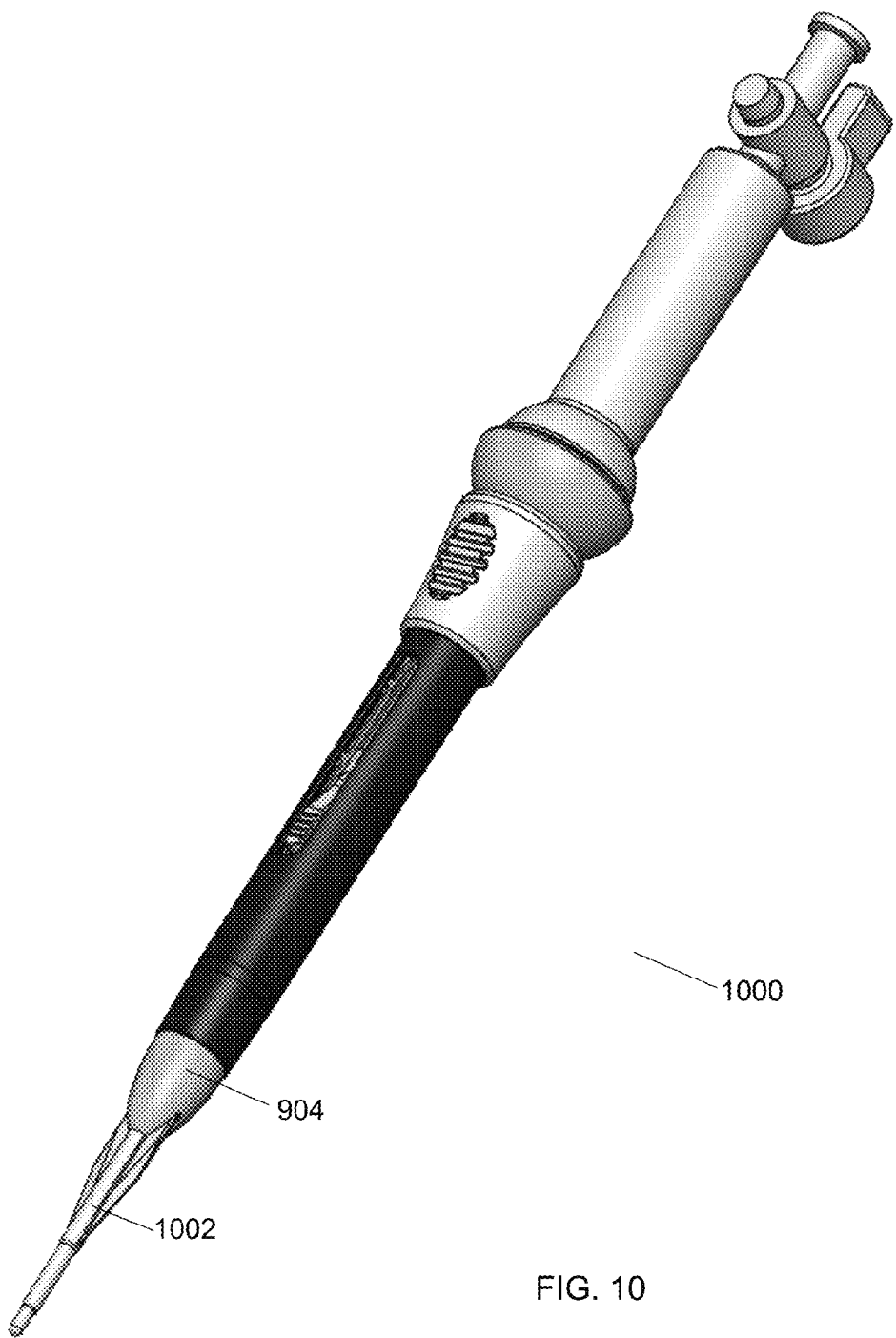

FIGS. 9-10 illustrate an alternate embodiment of an insertion device according to aspects of the present invention. As shown in FIG. 9, insertion device 900 includes dilator assembly 902, obturator assembly 904, and safety needle assembly 906. As shown in FIG. 10, insertion device 1000 includes blade assembly 1002.

Specific aspects of dilator assembly 902, obturator assembly 904, safety needle assembly 906, and blade assembly 1002 will be further described with reference to FIGS. 11-14.

Figure 11:
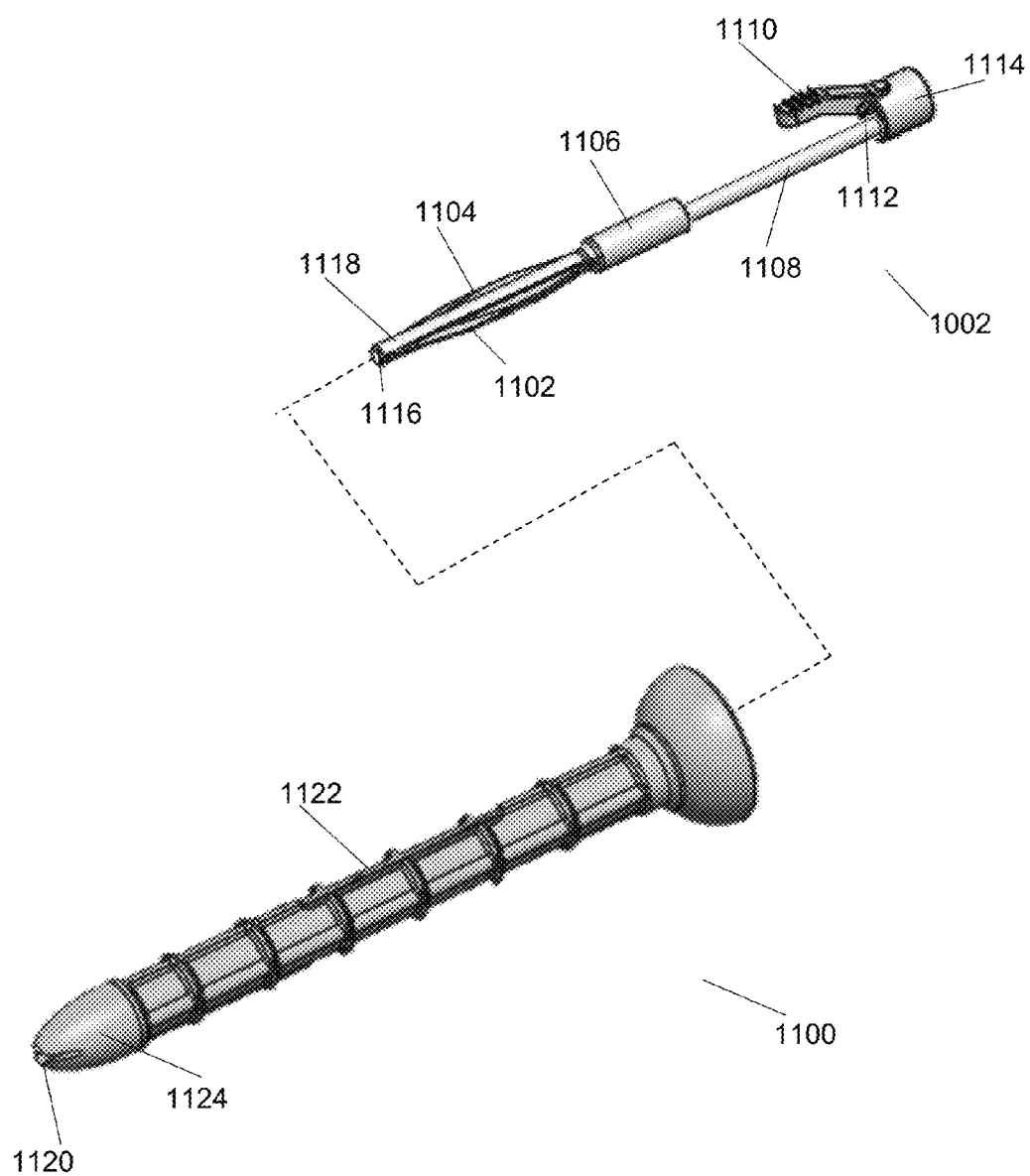
FIG. 11 illustrates the process by which an obturator assembly is assembled for an alternate embodiment of the insertion device.

FIG. 11 illustrates the process by which an obturator assembly is assembled for an alternate embodiment of the insertion device.

As shown in the figure, blade assembly 1002 includes blades 1102 and 1104, blade tube 1106, extension tube 1108, button 1110, lock 1112, cap 1114, lumen 1116, and shaft 1118. Obturator blank 1100 includes obturator tip 1124, blade slot 1120, and button slot 1122.

Shaft 1118 is a rigid tube and is preferably made of metal, however any other rigid material would suffice. Shaft 1118 is connected to blade tube 1106 such that there is no relative motion between the two components. The connection may be made via mechanical, adhesive, or chemical means. Shaft 1118 is also connected to blades 1102 and 1104. The connection is preferably a welded connection, however other connection means may be employed. As a non-limiting example, shaft 1118 may contain one or more slots at its distal end and blades 1102 and 1104 may contain one or more matching slots such that blades 1102 and 1104 may be assembled on to shaft 1118 by sliding slotted sections of blades 1102 and 1104 on to the corresponding slots at the distal end of shaft 302.

Blades 1102 and 1104 are preferably constructed from metal, more preferably from stainless steel, however any material suitable for medical applications would suffice. Blades 1102 and 1104 are operable to cut the skin of a patient, and as such are sufficiently sharp to cut skin. The specific shape, grind angles, and tip angles may be of any dimensions such that the effect of cutting skin may be accomplished. Blades 1102 and 1104 are attached to shaft 1118 as previously described.

Blade tube 1106 is a rigid tube and is preferably made of metal, however any other rigid material would suffice. Blade tube 1106 is connected to shaft 1118 as previously described, and blade tube 1106 is also connected to extension tube 1108 such that there is no relative motion between the two components. The connection may be made via mechanical, adhesive, or chemical means.

Extension tube 1108 is a rigid tube and is preferably made of metal, however any other rigid material would suffice. Extension tube 1108 is connected to blade tube 1106 as previously described, and extension tube 1108 is also connected to cap 1114 such that there is no relative motion between the two components. The connection may be made via mechanical, adhesive, or chemical means.

Cap 1114 is a rigid body and is preferably made of metal, however any other rigid material would suffice. Cap 1114 is operable to connect to extension tube 108 and to connect to button 1110.

Button 1110 is a deflectable body and is preferably made of any resilient material that can be deflected and then return to its original position. Button 1110 is connected to cap 1114 as previously described. Button 1110 also includes lock 1112, which protrudes from the side of button 1110 and is operable to secure blade assembly 1002 in a specific location. The operation of button 1110, lock 1112, and blade assembly 1002 will be further described with reference to FIGS. 13-14.

The individual components of blade assembly 1002 may all be manufactured separately and connected together as described above, but in alternate embodiments blade assembly 1002 may be a single, continuous component. In other alternate embodiments, various combinations of the individual components may be combined into single components for ease of manufacturing.

Obturator blank 1100 is preferably made from plastic via either machining or molding processes, however any suitable material or manufacturing method may be used to create the component. Obturator tip 1124 is operable to enlarge an opening in the skin, and includes blade slot 1120. Blade slot 1120 is operable to provide a pathway for blades 1102 and 1104 to be deployed beyond the distal-most portion of obturator tip 1124 and to be fully retracted within obturator tip 1124.

Button slot 1122 is an opening within the shaft of obturator blank 1100, and it is operable to provide an opening in which button 1110 may travel. The operation of button 1110 and its interaction with button slot 1122 will be further described with reference to FIGS. 13-14.

In operation, blade assembly 1002 is inserted into obturator blank 1100 to create obturator assembly 904. In some embodiments, obturator blank 1100 is created by molding 2 halves of the component that are not attached. The 2 halves may then be assembled around blade assembly 1002 before being connected by mechanical or chemical means.

Figure 12:
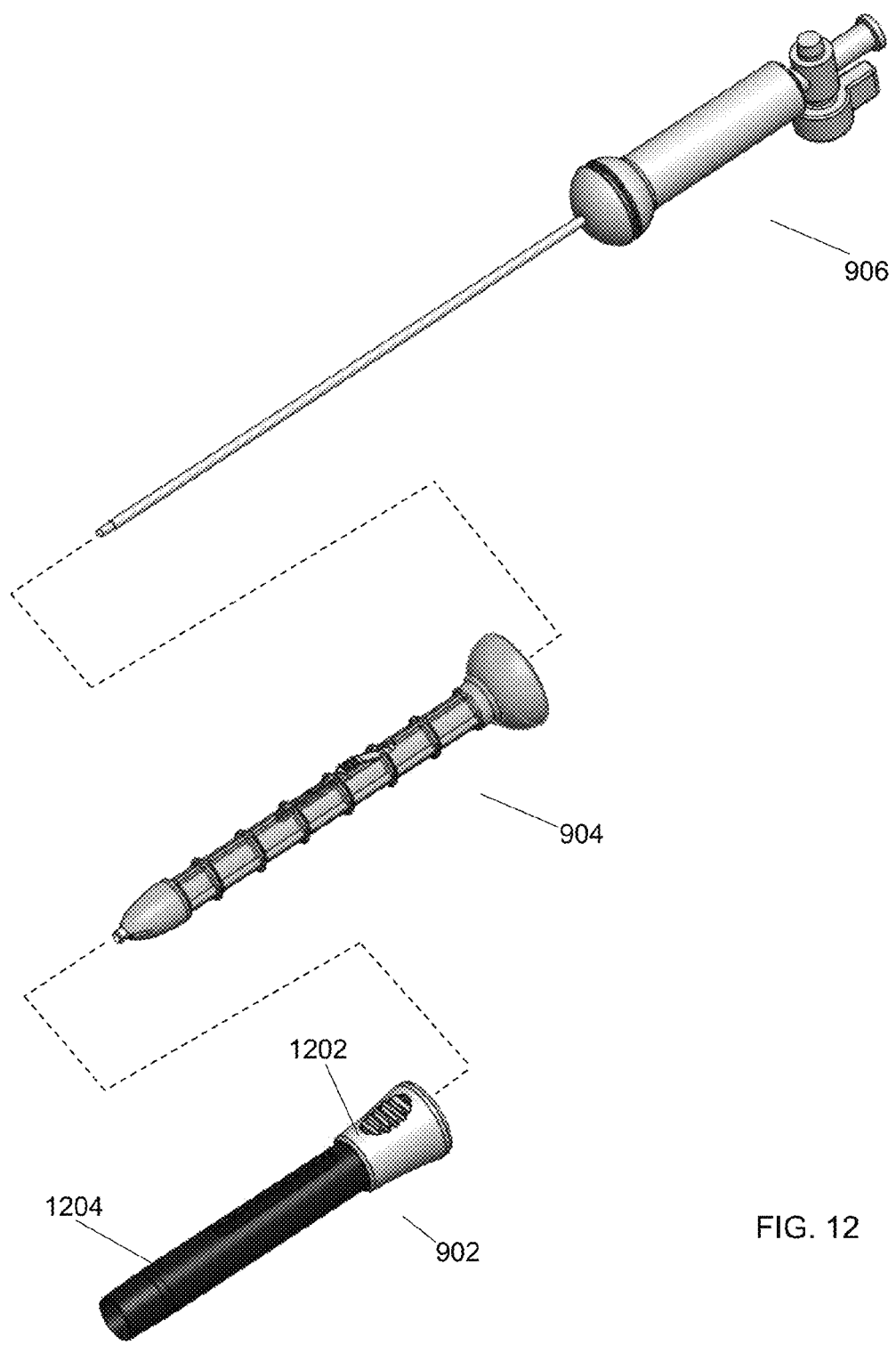
FIG. 12 illustrates the assembly process to create an alternate embodiment of the insertion device.

FIG. 12 illustrates the assembly process to create an alternate embodiment of the insertion device.

As shown in the figure, safety needle assembly 906 is inserted through obturator assembly 904. More specifically, safety needle assembly 906 is inserted through blade assembly 1002, which is part of obturator assembly 904. Safety needle assembly 906 is substantially similar in construction and operation to safety needle 102 from FIGS. 2, 6, and 7. Safety needle assembly 906 is releasably attached to obturator assembly 904 such that the components can be easily attached and detached. In some embodiments, and as a non-limiting example, there may be a tongue-in-groove connection between the two components such that a nominal amount of force is required to connect and disconnect, however in other embodiments there are no additional mechanisms to secure the components together.

The combination of safety needle assembly 906 and obturator assembly 904 is then inserted through dilator assembly 902. Dilator assembly 902 includes dilator shaft 1204 and dilator hub 1202. Dilator shaft 1204 is preferably made of plastic and may be extruded, molded, or manufactured in any other known way to create the desired geometry. Dilator hub 1202 is also preferably made of plastic by any known method to create the desired geometry. Dilator hub 1202 and dilator shaft 1204 are connected by any known methods that would serve to prevent any relative motion between the two components.

Obturator assembly 904 is releasably attached to dilator assembly 902 such that the components can be easily attached and detached. In some embodiments, and as a non-limiting example, there may be a tongue-in-groove connection between the two components such that a nominal amount of force is required to connect and disconnect, however in other embodiments there are no additional mechanisms to secure the components together.

Figure 13:
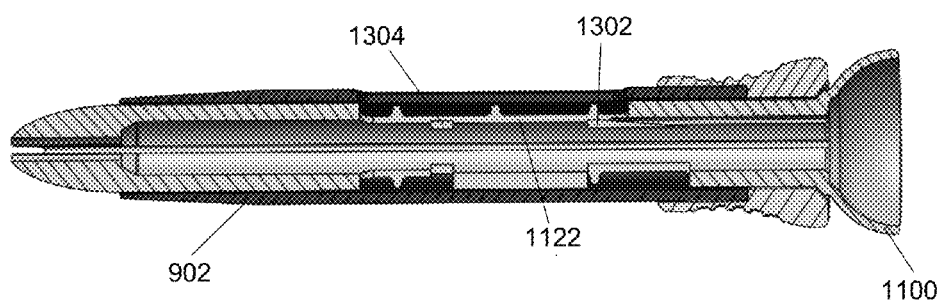
FIG. 13 illustrates a cross section of a dilator and an obturator of an alternate embodiment of the insertion device.

FIG. 13 illustrates a cross section of a dilator and an obturator of an alternate embodiment of the insertion device.

As shown in the figure, the cross section shows obturator blank 1100 assembled with dilator assembly 902. Obturator blank 1100 includes slots 1302 and 1304. Slots 1302 and 1304 are operable to mate with lock 1112 of blade assembly 1002.

Figure 14:
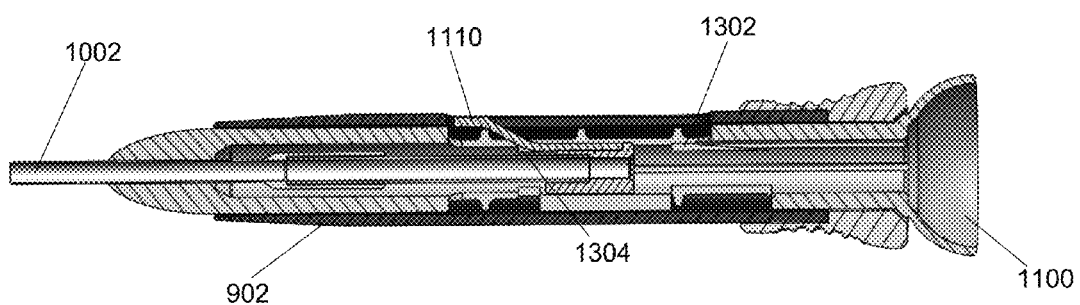
FIG. 14 illustrates a cross section of a dilator, obturator, and blade assembly of an alternate embodiment of the insertion device.

FIG. 14 illustrates a cross section of a dilator, obturator, and blade assembly of an alternate embodiment of the insertion device.

As shown in the figure, the cross section shows an assembly of obturator blank 1100, dilator assembly 902, and blade assembly 1002. Lock 1112 (not shown) is engaged with slot 1304, locking blade assembly 1002 in place. If the user desires to move blade assembly 1002, the user would deflect button 1110 (typically using finger pressure) to disengage lock 1112 from slot 1304. Then, keeping pressure on button 1110 to maintain it in the deflected position, the user would pull button 1110 back towards slot 1302 until slot 1302 engaged with lock 1112, thus locking blade assembly 1002 in a different position.

Operation of the device during a medical procedure will now be described with reference to FIGS. 9, 10, and 14. In a medical procedure, the user will receive the device with blades 1104 and 1102 in the retraced position, where lock 1112 is engaged with slot 1302. At this point, the only component protruding through obturator assembly 904 is safety needle assembly 906. After the doctor determines the appropriate place to insert the device, safety needle assembly 906 is inserted to the desired location in a manner similar to that described with reference to FIG. 6 and safety needle 102.

In order to create a larger incision in which dilator assembly 902 can fit, the user then depresses button 1110, disengaging lock 1112 from slot 1302. The user then advances button 1110 toward the distal end of the device, causing blade assembly 1002 to advance. When lock 1112 engages with slot 1304 the user releases button 1110, locking blade assembly 1002 in place, exposing blades 1102 and 1104. The user then advances the device until blades 1102 and 1104 enter the skin to create a skin nick. If desirable, after creating the first skin nick, the user may choose to pull the device back until blades 1102 and 1104 are not in the skin, rotate the device 90 degrees, and then advance the device again until blades 1102 and 1104 enter the skin again to create a second skin nick.

After the user creates the desired skin nicks, the user depresses button 1110, disengaging lock 1112 from slot 1304. The user then retracts button 1110 toward the proximal end of the device, causing blade assembly 1002 to retract, fully retracting blades 1102 and 1104 inside the device.

An advantage of this configuration is that it provides the ability of the user to actuate the blades with one hand, making the procedure more convenient compared to procedures performed with trocars requiring two hands to operate.

As described with reference to FIG. 7, the user will then advance obturator assembly 904 and dilator assembly 902 further into the patient while holding safety needle assembly 906 to prevent it from moving further into the patient. When the tip of obturator assembly 904 reaches the tip of safety needle assembly 906, the user may stop advancing the combination of obturator assembly 904 and dilator assembly 902. The user may use an appropriate imaging technique to determine when obturator tip 1124 reaches the tip of safety needle assembly 906. In an alternate embodiment, markers on the device may indicate when obturator tip 1124 reaches the tip of safety needle assembly 906, eliminating the need to use an imaging technique.

The user can then remove components to prepare the patient for insertion of a catheter. Safety needle assembly 906 and obturator assembly 904 may be removed from dilator assembly 902 at the same time, or separately as the user desires. To remove the components at the same time, the user would grip dilator assembly 902 with one hand and obturator assembly 904 with the other, and simply hold dilator assembly 902 still while pulling obturator assembly 904 until only dilatory assembly 902 is left in the patient. Alternatively, the user may first remove safety needle assembly 906, then remove obturator assembly 904.

As discussed with reference to FIG. 8, at this time, only dilator assembly is left in the patient, and the user will typically place a catheter through the lumen of the dilator shaft 1204 to reach the desired location in the body. Once the catheter is in the desired location, dilator assembly 902 is removed from the patient, and the user completes the procedure by closing the skin around the catheter.

The foregoing description of various preferred embodiments have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed as new and desired to be protected by Letters Patent of the United States is:

1. A device to access interior body regions comprising:
   a safety needle assembly operable to create a pathway through skin and into said interior body regions, said safety needle assembly further comprising a hub connected to a housing, a spring disposed within an open center of the housing, a cannula connected to said housing at a proximal end of said cannula, a stylet connected to said spring at a proximal end of said stylet, said stylet extending through an inner diameter of said cannula, said stylet further including a blunt stylet tip at a distal end of said stylet, wherein said blunt stylet tip is closed at said distal end of said stylet, and wherein said cannula includes a sharp cannula tip at a distal end of said cannula;

a blade assembly operable to cut tissue to create a skin nick and provide access into said interior body regions, said blade assembly further comprising at least one blade connected to a distal end of a blade shaft, a resilient button connected to a proximal end of said blade shaft, said resilient button including a lock, said blade shaft including a lumen with an inner diameter sized to allow said safety needle assembly to enter said lumen blade;

an obturator assembly operable to expand said pathway into said interior body regions, said obturator assembly releasably connected to said safety needle assembly and slidably coupled to said blade assembly, said obturator assembly further comprising a blade slot within an obturator tip and at least one slot, said blade slot sized and positioned to allow said at least one blade to extend through said blade slot;

a dilator assembly operable to maintain said pathway and provide access to said interior body regions, wherein said dilator assembly is releasably attached to said obturator assembly;

wherein said at least one slot is operable to engage with said lock such that when said at least one slot is engaged with said lock, said blade assembly cannot move relative to said obturator assembly;

wherein said spring is operable to bias said blunt stylet tip such that said blunt stylet tip is located distal to said sharp cannula tip when said spring is uncompressed; and wherein imparting a force to said blunt stylet tip causes said spring to compress.

2. The device of claim 1, wherein said at least one blade is not longitudinally coaxial with said safety needle assembly.

3. The device of claim 1, wherein said stylet further comprises at least one stylet port located proximal to a distal end of said safety needle assembly, said at least one stylet port extending from an outer diameter of said stylet through an inner diameter of said stylet, said at least one stylet port operable to contact body fluids within said interior body regions.

4. The device of claim 3, wherein said safety needle assembly further comprises a threaded connector attached to said hub, said threaded connector operable to receive a fluid drainage device such that fluid may be removed from said interior body regions via said at least one stylet port of said stylet to verify that said safety needle assembly is in the proper location within said interior body regions.

5. A method of accessing interior body regions, comprising:
providing an access device defining:
a safety needle assembly, a deployable and retractable blade assembly-slidably connected to an obturator assembly, and a dilator assembly, wherein said safety needle assembly, said blade assembly, and said obturator assembly are releasably attached to said dilator assembly;

advancing said safety needle assembly through a skin layer and into said interior body regions, creating a pathway from an outer surface of said skin layer and into said interior body regions;

unlocking at least one blade of said blade assembly by pressing and holding a button of said blade assembly, wherein said pressing and holding disengages a lock on said button from a first slot located on said obturator assembly;

deploying a said at least one blade of said blade assembly by sliding said button distally, wherein said sliding moves said blade assembly distally, causing said at least one blade to extend through a blade slot located in an obturator tip of said obturator assembly;

locking said at least one blade by releasing said button, wherein said releasing engages said lock with a second slot located distal to said first slot on said obturator assembly;

advancing said at least one blade of said blade assembly by pushing said obturator assembly toward said skin layer, cutting said skin layer near an outer diameter of said safety needle assembly to create a skin nick and increase the size of said pathway at said outer surface of said skin layer;

unlocking said at least one blade by pressing and holding said button, wherein said pressing and holding disengages said lock from said second slot;

retracting said at least one blade of said blade assembly by sliding said button proximally, wherein said sliding moves said blade assembly proximally, causing said at least one blade to retract through said blade slot such that said at least one blade cannot contact said skin layer;

locking said at least one blade by releasing said button, wherein said releasing engages said lock with said first slot;

advancing said blade assembly, said obturator assembly, and said dilator assembly through said skin nick, wherein said advancing comprises pushing said access device such that said obturator assembly further increases the size of said pathway deeper than said outer surface of said skin layer; and disconnecting said blade assembly, said safety needle assembly, and said obturator assembly from said dilator assembly, leaving said dilator assembly within said pathway to provide access to said interior body regions.

6. The method of claim 5, further comprising confirming said safety needle assembly is in a desired location prior to said advancing of said blade assembly.

7. The method of claim 6, wherein said confirming comprises connecting a fluid drainage device to said safety needle assembly, draining fluid from said interior body regions, and using said fluid to determine if said safety needle assembly is in the desired location.

* * * * *